US012023012B2

(12) United States Patent
Jean-Baptiste et al.

(10) Patent No.: US 12,023,012 B2
(45) Date of Patent: Jul. 2, 2024

(54) SELF-RETAINING MEDICAL RETRACTOR TO FACILITATE SURGICAL PROCEDURES AND INSPECTION

(71) Applicants: Shayne Jean-Baptiste, St Petersburg, FL (US); Stephanie Jean-Baptiste, St Petersburg, FL (US)

(72) Inventors: Shayne Jean-Baptiste, St Petersburg, FL (US); Stephanie Jean-Baptiste, St Petersburg, FL (US)

( * ) Notice: Subject to any disclaimer, the term of this patent is extended or adjusted under 35 U.S.C. 154(b) by 0 days.

(21) Appl. No.: 17/895,931

(22) Filed: Aug. 25, 2022

(65) Prior Publication Data

US 2024/0065541 A1 Feb. 29, 2024

(51) Int. Cl.
  *A61B 1/32* (2006.01)
  *A61B 17/00* (2006.01)
  *A61B 17/02* (2006.01)

(52) U.S. Cl.
  CPC ............ *A61B 1/32* (2013.01); *A61B 17/0206* (2013.01); *A61B 2017/00429* (2013.01); *A61B 2017/00858* (2013.01); *A61B 2017/00889* (2013.01); *A61B 2017/00955* (2013.01)

(58) Field of Classification Search
  CPC ................................ A61B 1/32; A61B 17/0206
  USPC ................................................. 600/201–245
  See application file for complete search history.

(56) References Cited

U.S. PATENT DOCUMENTS

| | | | | |
|---|---|---|---|---|
| 3,841,318 A | * | 10/1974 | Olson | A61M 29/02 606/210 |
| 8,287,565 B2 | * | 10/2012 | Risto | A61B 17/02 606/206 |
| 2011/0077468 A1 | * | 3/2011 | Finger | A61B 17/0231 600/236 |
| 2023/0190252 A1 | * | 6/2023 | Deuel | A61B 17/00234 600/104 |

* cited by examiner

*Primary Examiner* — Eduardo C Robert
*Assistant Examiner* — Tara Rose E Carter
(74) *Attorney, Agent, or Firm* — The Rapacke Law Group, P.A.; Andrew S. Rapacke (57) ABSTRACT

A self-retaining retractor that facilitates surgical procedures and inspection by a surgeon and eliminates the need for surgical assistance. The self-retaining retractor includes a hinge, a pair of curved arms, a pair of perpendicular arms, and a plurality of fingers emulating from each pair of perpendicular arms. Each of the pair of curved arms includes an upper portion and a lower portion. The near end of the lower portion of the each of the pair of curved arms is coupled to the hinge. The near end of each of the pair of perpendicular arms is coupled to the distal end of the upper portion of the each of the pair of curved arms.

18 Claims, 10 Drawing Sheets

SELF-RETAINING MEDICAL RETRACTOR TO FACILITATE SURGICAL PROCEDURES AND INSPECTION

FIELD

The present disclosure relates to a self-retaining medical retractor that facilitates surgical procedures and inspections by a surgeon and eliminates the need for surgical assistance, and more particularly to a vaginal vault retractor for improved vaginal and perineal exposure that enhances safety for the patient, surgeon, and surgical assistants during medical procedures.

BACKGROUND

A retractor is a surgical instrument used to separate and manipulate the edges of a surgical incision or wound, or to hold back underlying organs and tissues so that body parts underneath may be accessed.

SUMMARY

Vaginal vault retractor used for exposure of perineum and distal vagina. While in the closed position, the upper portion of the vaginal vault retractor is placed about 4 cm into the vaginal vault. The vaginal vault retractor is then opened on a pivot perpendicular to the vagina canal, opening laterally, to expose underlying tissue to allow for procedures such as repair of vaginal tears, episiotomies, vulvar and distal vaginal biopsies, excisional biopsies, and the like. The vaginal vault retractor has smooth notches to prevent slippage of tissue while gently holding upper portion of the vaginal vault retractor in place. The pivot of the vagina vault retractor is a smooth slide with tightening screw to allow flexibility, while the pivot arms or outer handle are curved outwards as to not obstruct underlying tissue.

In various embodiments, a self-retaining vaginal vault retractor used by surgeons to facilitate surgical procedures and inspections is provided. The vaginal vault retractor includes a hinge, a pair of curved arms, a pair of perpendicular arms, and a plurality of fingers emulating from each pair of perpendicular arms. Each of the pair of curved arms includes an upper portion and a lower portion. The near end of the lower portion of the each of the pair of curved arms is coupled to the hinge. The near end of each of the pair of perpendicular arms is coupled to the distal end of the upper portion of the each of the pair of curved arms.

In various embodiments, the lower portion each of the pair of curved arms is configured to rest on the perineum and provide and an unobstructed view of the vaginal vault. In contrast, to the lower portion each of the pair of curved arms, the plurality of fingers emulating from each pair of the perpendicular arms are configured to be placed within the vaginal vault.

In various embodiments, each of the plurality of fingers has a shape that is substantially the same as the shape of the upper portion of each of the pair of curved arms.

In various embodiments, the pair of curved arms are configured to open perpendicular to the vaginal vault.

In various embodiments, each of the plurality of fingers is made of a material having a high coefficient of friction.

In various embodiments, one or more of the pair of curved arms, the pair of perpendicular arms, and the plurality of fingers is made of a polyether ether ketone (PEEK) material. In some embodiment, the PEEK material is configured to have antimicrobial properties.

In various embodiments, one or more of the pair of curved arms, the pair of perpendicular arms, the plurality of fingers, and the hinge is made of a nylon material. For example, one or more of nylon 6, nylon 6/6, nylon 12, and the like. In some embodiments, the hinge is made of one or more of oil-filled nylon, molybdenum disulfide-filled nylon, and the like.

In various embodiments, one or more of the pair of curved arms, the pair of perpendicular arms, the plurality of fingers, and the hinge is made of a thermoplastic material. For example, one or more of polycarbonate, polypropylene, polyethylene, and the like.

In various embodiments, the pair of curved arms form a lemniscate shape having a gap in the middle when the pair of curved arms are in the closed position.

In various embodiments, the pair of curved arms form a pair of oval apertures. A lower oval aperture that is proximate to the hinge and an upper oval aperture that is distal to the hinge. The lower oval aperture and the upper oval aperture are in fluid communication and the size of the lower oval aperture is larger than the size of the upper oval aperture.

In various embodiments, the hinge is configured to be located below the vaginal vault. In some embodiments, the hinge is configured to be located above the vaginal vault.

In various embodiments, the lower portion of each of the pair of curved arms forms a handle. In some embodiments, the handle is coated with a material having a high coefficient of fiction configured to make the handle easier to grip and manipulate In various embodiments, a portion of the handle extends beyond the hinge to form an extended handle. The extended handle comprises a loop configured to make the extended handle easier to grip and manipulate.

In various embodiments, the shape of the plurality of fingers emulating from each pair of perpendicular arms have a shape that is configured to increase the static coefficient of friction between the plurality of fingers and the vaginal vault. In some embodiments, the plurality of fingers emulating from each pair of perpendicular arms form a linear series of elongated ridges.

In some embodiments, the hinge comprises first hinge leaf having spaced-apart knuckles and a second hinge leaf having a single knuckle configured to fit between the spaced-apart knuckles of the first hinge leaf. The spaced-apart knuckles and the single knuckle comprise an aligned knuckle cavity(s) formed by an aligned longitudinal knuckle aperture(s). The hinge further comprises a hinge pin or fastener configured to inserted into the aligned knuckle cavity(s) having a first end portion that is greater in diameter than the aligned knuckle cavity(s). A length of the hinge pin is slightly shorter than a length of the aligned knuckle cavity(s) and comprises a hinge pin cavity formed by a longitudinal hinge pin aperture. The end of the hinge pin cavity proximate to a second end portion of the hinge pin is thread and configured to receive a fastener having a mating thread. The fastener is operable as an adjustable friction brake. That is, by tightening the fastener the spaced-apart knuckles are deformed to reducing a spacing between the spaced-apart knuckles and increasing a compression force on a single knuckle configured to fit between the spaced-apart knuckles. In some embodiments, the fastener is a flat headed and recessed screw that is configured to allow smooth adjustments after placement.

In various embodiments, the hinge further comprises a frictional brake. The friction brake can be used to adjust the friction level when the curved arm(s) 120 are rotated. In some embodiments, the pair of curved arms are configured to have a range of rotation of about 90 degrees and below. In some embodiments, the frictional brake is configured to clamp the pair of curved arms in a static position within the range of rotation to prevent inadvertent movement during a surgical procedure or viewing. The curved arms are configured to curve outwards to not obstruct the view of the underlying tissue during evaluation and surgical procedures.

In various embodiments, the frictional brake includes a locking screw which is configured to adjust the level of friction for the hinge. In some embodiments the locking screw is configured to clamp the pair of curved arms in a static position within the range of rotation.

In various embodiments, the hinge includes one or more of a leaf spring, a torsion, and a web operable to push the pair of curved arms to an open position.

In various embodiments, the hinge includes a stop configured to arrest a rotation of the pair of curved arms.

In various embodiments, the vaginal vault retractor includes a hinge. The hinge includes a first hinged member having a pair of spaced-apart knuckles and a second hinged member having a single knuckle configured to fit between the pair of spaced-apart knuckles. The vaginal vault retractor also includes a first curved handle having a first near end couped to the first hinged member and a second curved handle having a second near end coupled the second hinged member. The first curved handle and the second curved handle form an aperture with an hourglass shape having a bust and a hip. The size of the bust is greater than the size of the hip. The vaginal vault retractor also includes a first wing coupled to a first distal end of the first curved handle and a second wing coupled to a second distal end of the second curved handle.

In various embodiments, a vaginal vault retractor includes a pair of hinged curved arms having a near end and a distal end. The near ends of the pair of hinged curved arms are flexibly coupled by a hinge. The pair of hinged curved arms form a shape of an upright lemniscate. The vaginal vault retractor also includes a perpendicular arm having plurality of fingers coupled the distal end of each of the pair of hinged curved arms. The vaginal vault retractor also includes a locking screw. The locking screw can be configured to adjust a level of friction for the rotation of the pair of hinged curved arms or arrest the rotation of the pair of hinged curved arms.

Additional features and advantages of the embodiments disclosed herein will be set forth in the detailed description that follows, and in part will be clear to those skilled in the art from that description or recognized by practicing the embodiments described herein, including the detailed description which follows, the claims, as well as the appended drawings.

Both the foregoing general description and the following detailed description present embodiments intended to provide an overview or framework for understanding the nature and character of the embodiments disclosed herein. The accompanying drawings are included to provide further understanding and are incorporated into and constitute a part of this specification. The drawings illustrate various embodiments of the disclosure, and together with the description explain the principles and operations thereof.

BRIEF DESCRIPTION OF THE DRAWINGS

The features and advantages of the present disclosure will be more fully described in, or rendered obvious by, the following detailed description of the preferred embodiments, which are to be considered together with the accompanying drawings, wherein like numbers refer to like parts and further, wherein.

DETAILED DESCRIPTION

Reference will now be made in detail to the present preferred embodiment(s), examples of which is/are illustrated in the accompanying drawings. Whenever possible, the same reference numerals will be used throughout the drawings to refer to the same or like parts.

Figure 1:
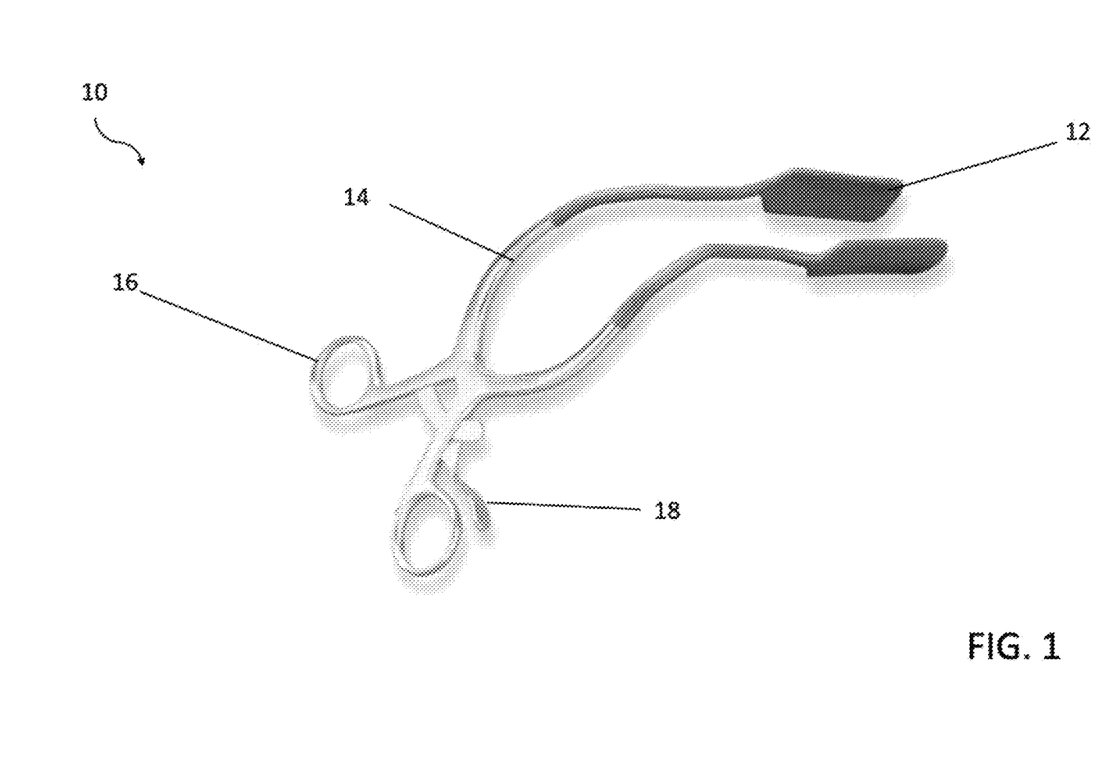
FIG. 1 is a top perspective view of a vaginal retractor.

FIG. 1 shows a top perspective view of a vaginal retractor 10. The vaginal retractor 10 comprises a pair of hinged arms 14. Each of the pair of hinged arms 14 has a distal end terminated with a flat blade 12 and a near end terminated with a looped handle 16. The vaginal retractor 10 of FIG. 1 is not self-retaining and has to be held in place by a surgical assistant. While it is not uncommon for the vaginal retractor 10 to be available in range of blade sizes, these blade sizes are normally greater than 50 mm. Standard blade lengths include 50 mm, 75 mm, and 100 mm. That is, the conventional speculum 10 is configured for deeper access than the proposed vaginal vault retractor 100 and requires a surgical assistant to retain it in place. Further, the available blade lengths obstruct the surgeon's access and view of features that nearer than at least 50 mm. Based on the shape and orientation of flat blade 12, the flattened parts are used for distal retraction of the vagina closer to the cervix once placed during a medical procedure. Due to the retraction of deeper vaginal tissue, this type of vaginal retractor 10 does not adequately allow for exposure of superficial vaginal tissues and perineum.

Figure 7A:
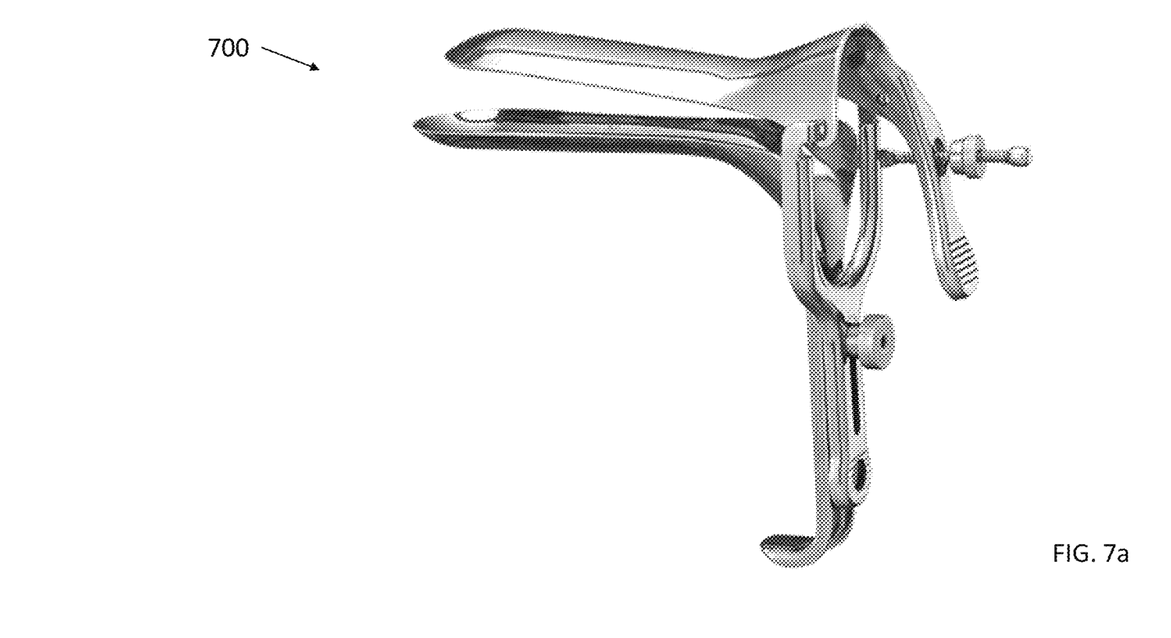
FIG. 7a illustrates a perspective view of a conventional speculum.
Figure 7B:
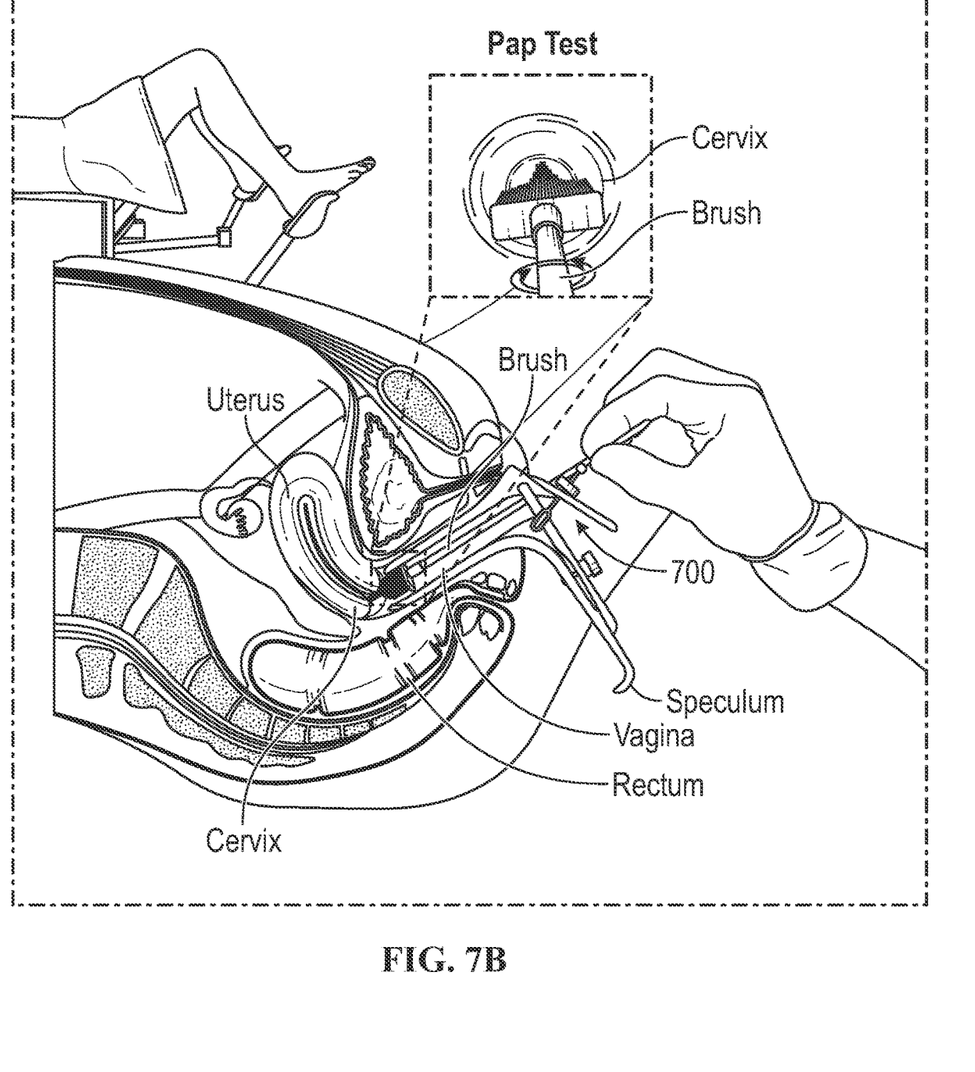
FIG. 7b illustrates a cutaway view of a conventional speculum being used in a medical procedure.

FIG. 7a illustrates a perspective view of a conventional speculum 700 and FIG. 7b illustrates a cutaway view of a conventional speculum 700 being used in a medical procedure. Similar to problems with a weighted speculum, a traditional speculum obstructs the tissue of the perineum and does not provide adequate exposure to the distal vaginal landmarks and perineum. Conventional speculum 700 is used to visualize deeper portions of the vaginal canal when rotated, as these portions are visible through slits in each side of conventional speculum 700. Primarily, conventional speculum 700 provides access to deeper vaginal vault and cervix.

Figure 8:
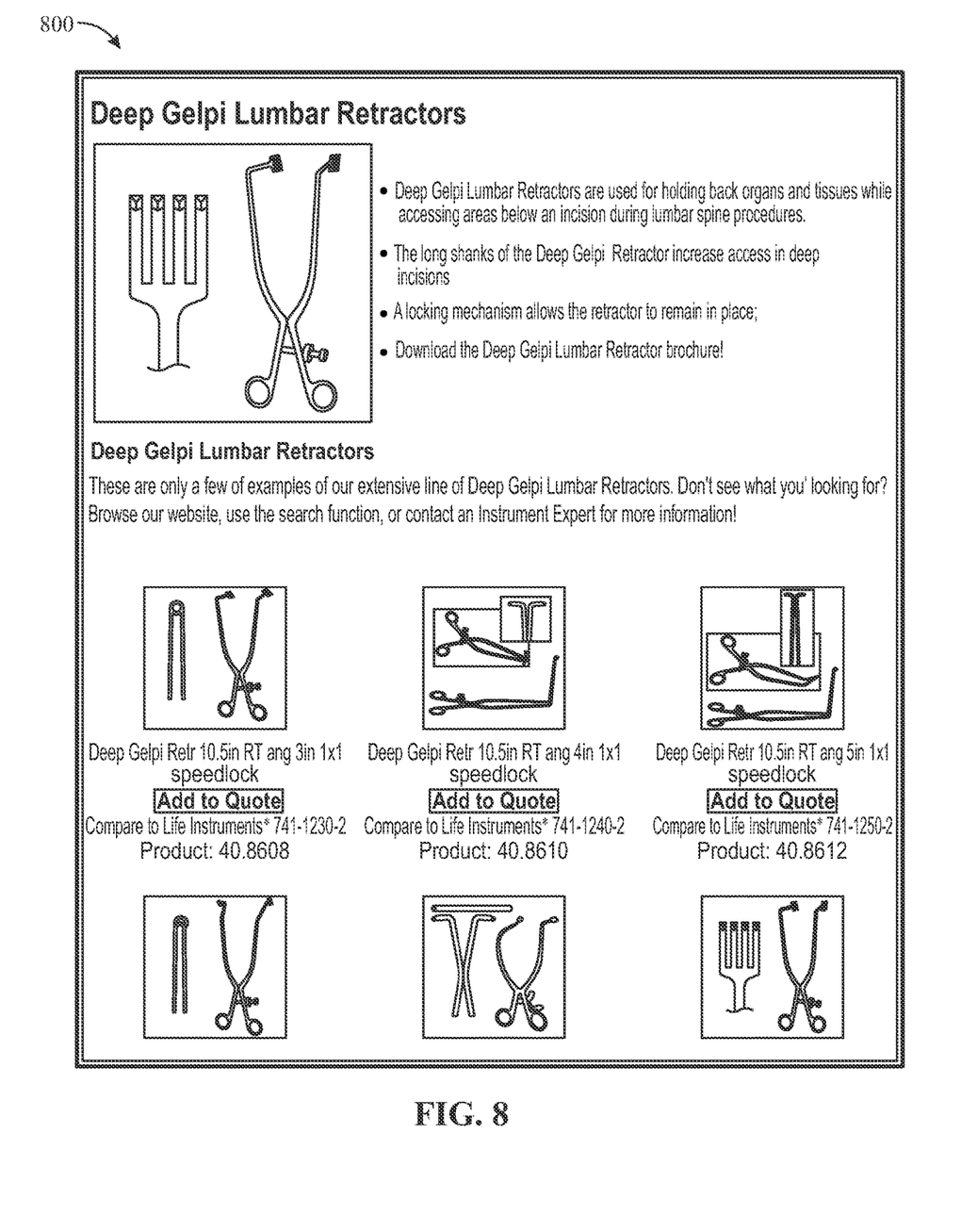
FIG. 8 illustrates a variety of Gelpi lumbar retractors.

FIG. 8 illustrates a variety of Gelpi lumbar retractors 800. It should be understood that Gelpi retractors are used in orthopedic cases to retract the lumbar tissues. While some similarities exist between Gelpi lumbar retractors and vaginal vault retractors described herein, Gelpi lumbar retractors include hooks that are generally used to hold the instrument in place. This makes Gelpi retractors particularly ill suited for vaginal examination and procedures as such hooks would have a traumatic and devastating effect on vaginal tissue and could result in further injury and bleeding.

Figure 2:
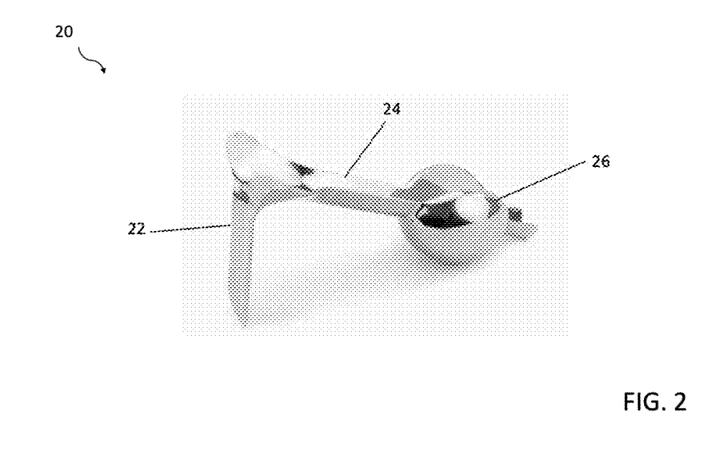
FIG. 2 is a side perspective of conventional weighted speculum.

FIG. 2 shows a side perspective of conventional weighted speculum 20. The weighted convention speculum 20 comprises a single arm 24. The single arm 24 has a distal end terminated with a large substantially flat blade 12 and a near end terminated with a large weight 22. The large substantially flat blade 12 has a shape analogous to that of a duckbill and is normally used to view the vagina canal 200. The conventional weighted speculum 20 of FIG. 2 is self-containing and does not have to held in pace by a surgical assistant. While it is not uncommon for the conventional weighted spectrum 10 to be available in range of sizes, these blade sizes are normally greater than 50 mm, not least because the blade must be substantial to support the large weight which is about 2½ lbs. That is, the conventional weighted speculum 20 is configured for deeper access than the proposed vaginal vault retractor 100. Further, the heavy construction of the conventional weighted speculum 20 obstructs the surgeon's access and view.

Figure 3:
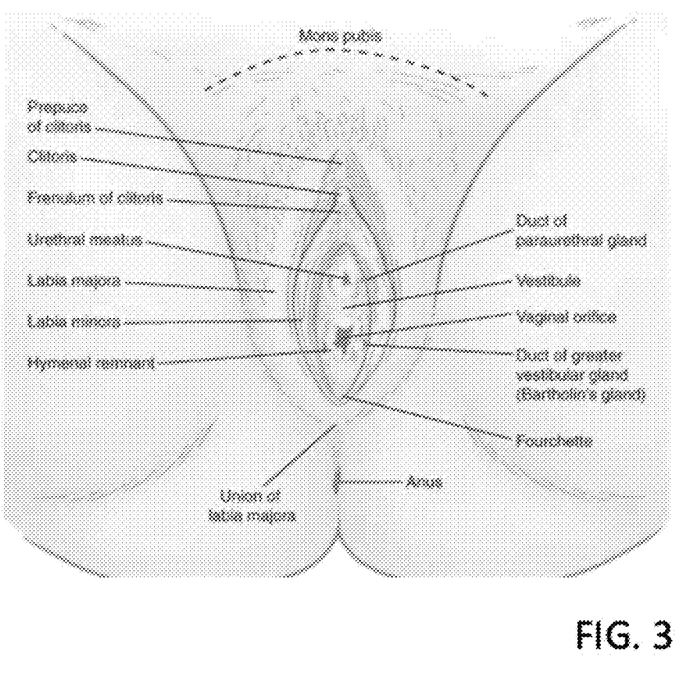
FIG. 3 is a front view of vulvar anatomy.

FIG. 3 shows a front view of vulvar anatomy landmarks described herein.

Figure 4:
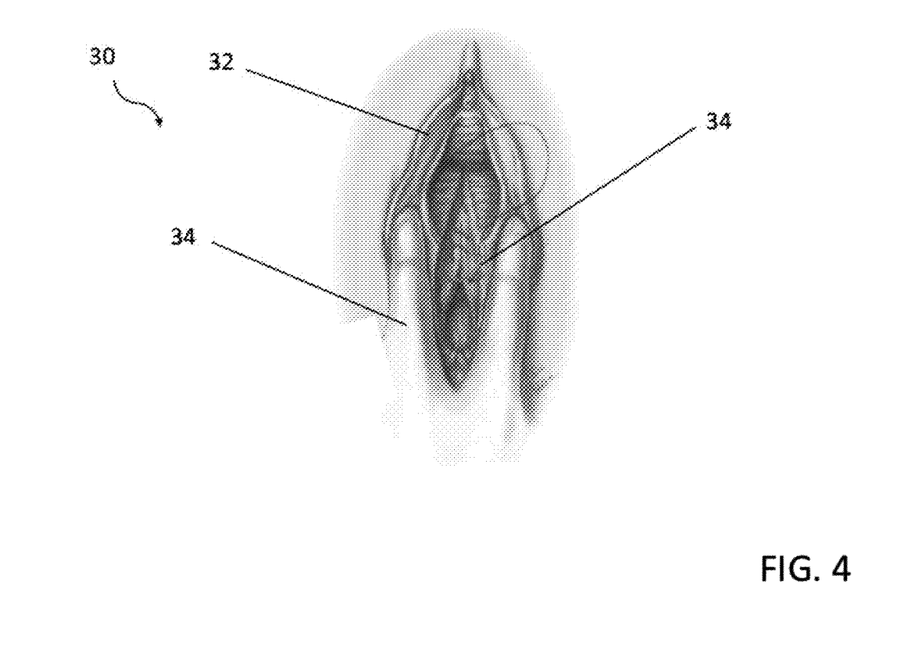
FIG. 4 is a front view illustrating the manual manipulation of tissue as an alternative to vaginal retractors and conventional speculums illustrated in FIG. 1 and FIG. 2.

FIG. 4 shows the manual manipulation of tissue as an alternative to conventional speculums such as those illustrated in FIG. 1 and FIG. 2. Conventional speculums allow greater access to deeper vaginal landmarks, such as the upper ⅓ of the vagina and the cervix. However, these conventional speculum provide limited or no view of the lower vagina, vulva, and perineum. Therefore, current methods of gaining access to the perineum and outer vagina for surgical procedures and inspections are in practice reliant either the surgeon or their assistant using their fingers to manually manipulate and separate tissue. This practice is unsafe because it exposes fingers to needles, scalpels, and the like. The use of convention speculums 10, such as those show in FIG. 1 prohibit accessibility to the outer portion of vagina and ability to safely retract tissue during a surgical procedure. Alternatives, to the convention speculum 10 of FIG. 1 include the conventional weighted speculum 20 of FIG. 2. These conventional weighted speculums 20 are more commonly found in the operating suite, at least because they are not suitable for patients who are awake. The conventional weighted speculum 20 also block viewing and access to posterior portion of the vaginal and vulva. The use of alternative medical instruments, such as right angle retractors, or Deaver retractors, requires a surgical assistant to hold two retractors during the procedure are again poorly tolerated by patients who are awake. As such, these devices like the conventional weighted speculum are generally restricted to the operating suite where they are used under general anesthesia.

Figure 5:
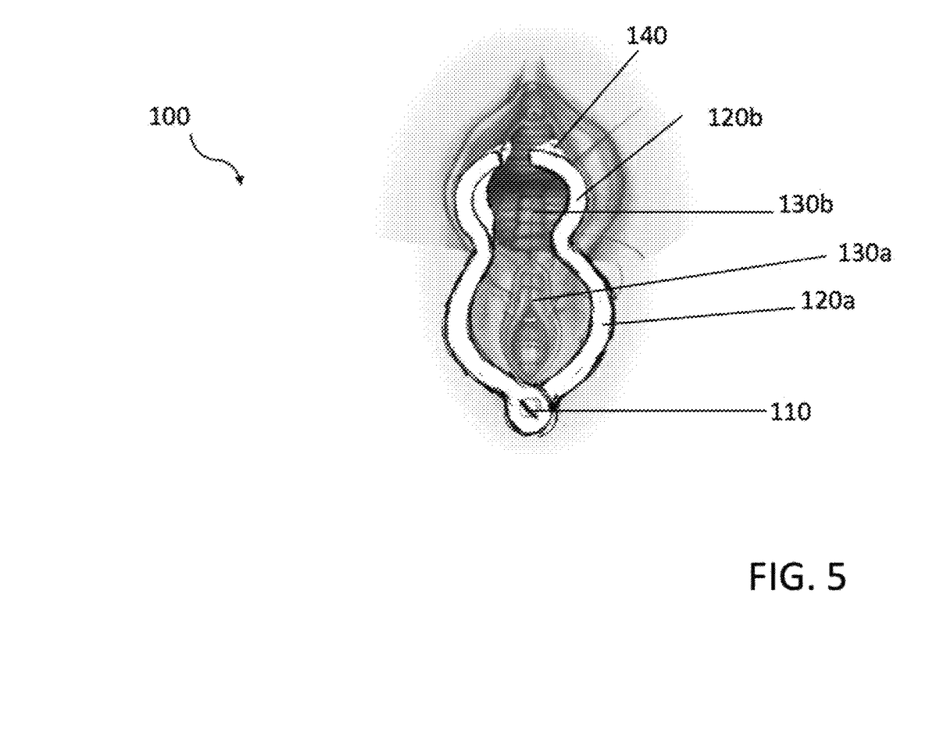
FIG. 5 illustrates an improved method of retraction and exposure utilizing the proposed vaginal vault retractor, in accordance with some embodiments described herein.

FIG. 5 shows an improved method of retraction and exposure utilizing the proposed vaginal vault retractor 100.

In various embodiments, the vaginal vault retractor 100 comprises two curved arms 120 coupled by a hinge 110. The hinged pair of curved arms 120 form a shape that is similar or analogous to a figure-eight or a lemniscate shape when the two hinged and curved arms 120 are in a closed position. That is, the two hinged and curved arms 120 form a pair of oval like apertures 130, a lower aperture 130a and an upper aperture 130b, when in a closed position. The lower aperture 130a being nearer the base or hinge 110 of the vaginal vault retractor 100 and the upper aperture being further away from the base or hinge 110 of the vaginal vault retractor 100. In various embodiments, the lower aperture 130a and the upper aperture 130b are fluidity connected when the two hinged and curved arms 120 are in the closed position. In various embodiments, a size of the lover aperture 130a is greater than or equal to a size of the upper aperture 130b. One or more of the lower aperture 130a and the upper aperture 130b may have an oval shape, which is a shape that resembles that of an egg. One or more of the lower aperture 130a and the upper aperture 130b may have an ellipse shape, a circular shape, an oblong shape, and the like.

In various embodiments, the distal end of each of the curved arms 120 comprises a perpendicular arm 140 that is substantially perpendicular to the upper portion 120b of the curved arms 120. In some embodiments, the length of the perpendicular arm 150 is about 40 mm and below A plurality of fingers 150 emulate from the perpendicular arm 140. Each of the fingers 150 having a shaped that is similar to that of the upper portion 120b of the curved arms 120. At least the perpendicular arm 140 and the plurality of fingers 150 emulating from the perpendicular arm 140 are configured to be placed within the vagina 200 vault. In various embodiments, the plurality of fingers 150 emulating from the perpendicular arm 140 are smooth ridges, or form an elongate structure configured 150 to allow for gentle intravaginal traction. In some embodiments, the smooth ridges form a linear series of elongated ridges.

In various embodiments, only the upper portion 120b of the vaginal vault retractor 100 is configured to be placed with the vaginal vault 200. The lower portion 110a of the vaginal vault retractor 100 is configured to rest the perineum thereby allowing an unobstructed view of the vaginal vault 200. In some embodiments, the lower portion 120a of the vaginal vault retractor 100 are the bottom of the curved arms 120 that are configured to rest on the perineum while providing the surgeon with an unobstructed view of the vaginal vault 200.

In various embodiments, the pivot point formed by the hinge 110 for the pair of curved arms 120 is situated at the base of the vaginal vault retractor 100. In some embodiments, the pivot point is located at the top of the vaginal vault retractor 100 (not shown). The upper portion 120b of the vaginal vault retractor 100 is located furthest from the hinge 110 and the lower portion 120a of the vaginal vault retractor 100 is located nearest the hinge 110.

In some embodiments, the hinge 110 further comprises a torsion spring having a first end coupled to the first member or first curved arm 120 and a second end coupled to the second member or second curved arm 120. A torsion spring is a helical spring that exerts a torque or rotary force. The ends of the torsion spring are attached to other components, and when these components rotate around the center of the torsion spring, the spring is configured to push the components back to their original positions. In some embodiments, the torsion spring is configured to work in a clockwise direction. That is, the torsion spring is configured to apply a rotational force that cause the two members to separate.

In some embodiments, the hinge 110 further comprises a leaf spring having a first end coupled to the first member or first curved arm 120 and a second end coupled to the second member or second curved arm 120. The leaf spring comprises a strip of metal that is curved slightly upwards. In some embodiments, the leaf spring comprises a number of strips of metal curved slightly upwards and clamped together in a stacked or laminated arrangement.

In some embodiments, the hinge 110 further a rotatory ratchet configured to allow rotation in one direction and allow rotation in another direction, and wherein the rotatory ratchet comprises a release mechanism. For example, the release mechanism may be spring loaded button, lever, and the like.

In some embodiments the friction brake further comprises a first adjustment screw located on a first end of the hinge 110 and a second adjustment screw located on the second end of the hinge 110. The first adjustment screw is configured to constrain the range of motion of the hinge 110 and the second adjustment screw is configured to adjust the resistance to rotational motion. In various embodiments, the hinge 110 is configured to have little if any radial play in the locked position and no axial play in any position. The first adjustment screw and the second adjustment screw have one or more distinguishable features. For example, the first adjustable screw and the second adjustable screw are color coded, numbered, labeled, and the like.

In various embodiments, the friction is configured by interlocking two friction cones that can be adjusted as needed with the fastener 115. The two friction cones provide a large friction surface. In some embodiments, the cones are made of a low-wear plastic material.

In various embodiments, the hinge 110 comprises a first mechanism to adjust the resistance to motion and a second mechanism to adjust the range of motion. In some embodiments, the means to adjust the first mechanism and the second mechanism are concentric. For example, a lever attached to the barrel of the hinge 110 and a screw located within the lever and aligned with the barrel.

In some embodiments, the hinge 110 is a living hinge constructed form a soft flexible material having excellent fatigue resistance, for example nylon 12. Nylon 12 is a good general-use plastic with broad additive applications and is known for its toughness, tensile strength, impact strength and ability to flex without fracture. It is this ability to flex without fracture that makes nylon 12 suitable for the at least the hinge 110 portion of the vaginal vault retractor 100. The living hinge may also be made from acrylonitrile butadiene styrene. In some embodiments, at least the outer portion of the hinge 110 is smooth and forms an uninterrupted surface with the parent material. For example, the curved arms 120.

In some embodiments, the hinge 110 further comprises one or more webs operable to push the pair of curved arms 120 to an open position or pull the pair of curved arms 120 to the closed position. That is, the hinge 110 is bi-stable hinge that is configured to either snap to the open position or snap the closed position. A web acts like a spring that is configured to push two rigid elements to an open position or pull two rigid elements to a closed position. In some embodiments, the one or more webs are configured to allow only a range of motion while disallowing others.

Figure 6A:
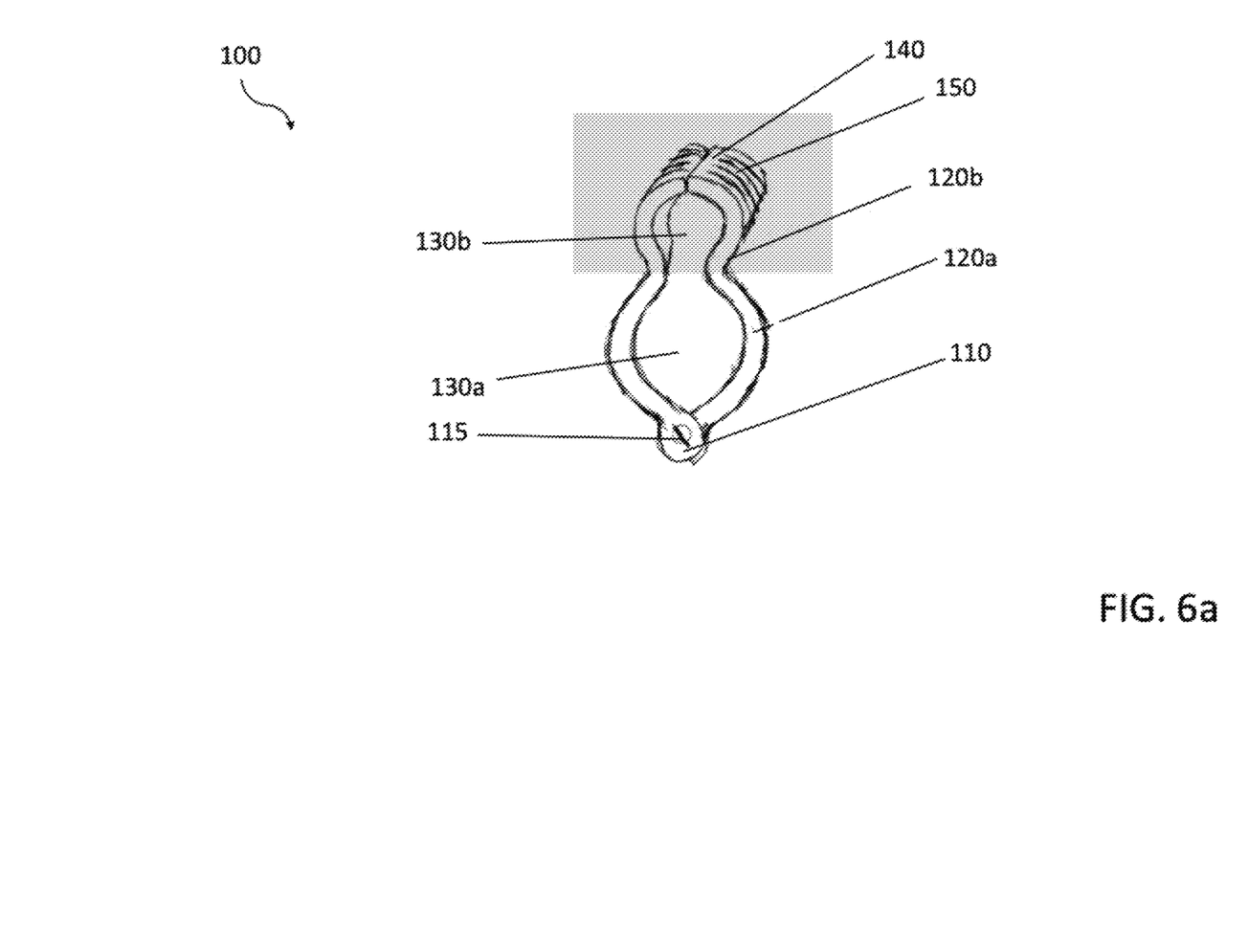
FIG. 6a illustrates the proposed vaginal vault retractor in the closed position, in accordance with some embodiments described herein.

FIG. 6a shows the vaginal vault retractor 100 in the closed position.

The vaginal vault retractor 100 will be used for retraction of perineum and distal vaginal canal 200 to allow exposure of tissue to allow for safe patient and surgeon procedures on the distal portion of vaginal canal 200 and perineum. The vaginal vault retractor 100 is placed into the vaginal canal 200, opening laterally, to expose underlying tissue to allow for procedures such as repair of vagina tears, episiotomies, vulvar and distal vaginal biopsies, and excisional and excisional biopsies. The vaginal vault retractor 100 has smooth notches on the upper portion to prevent slippage of tissue while gently holding the vaginal vault retractor 100 in place.

In some embodiments, the hinge 110 comprises first hinge leaf having spaced-apart knuckles 110a and a second hinge leaf having a single knuckles configured to fit between the spaced-apart knuckles 110b of the first hinge leaf. The spaced-apart knuckles 110a and the single knuckle 110b comprise an aligned knuckle cavity(s) formed by an aligned longitudinal knuckle aperture(s). The hinge 110 further comprises a hinge pin configured to inserted into the aligned knuckle cavity(s) having a first end portion that is greater in diameter than the aligned knuckle cavity(s). A length of the hinge pin is slightly shorter than a length of the aligned knuckle cavity(s) and comprises a hinge pin cavity formed by a longitudinal hinge pin aperture. The end of the hinge pin cavity proximate to a second end portion of the hinge pin is thread and configured to receive a fastener 115 having a mating thread. The fastener 115 is operable as an adjustable friction brake. That is, by tightening the fastener 115 the spaced-apart knuckles 110a are deformed to reducing a spacing between the spaced-apart knuckles 110a and increasing a compression force on a single knuckle 110b configured to fit between the spaced-apart knuckles 110a. In some embodiments, the fastener 115 is a flat headed and recessed screw that is configured to allow smooth frictional adjustments after placement.

In some embodiments, the fastener 115 is a lever, a flat headed screw, a TORX screw, Allen key screw, and the like.

In various embodiments, at least a portion of the vaginal vault retractor 100 is made of a nylon material. For example, one or more of the two curved arms 120, perpendicular arm 140, and plurality of fingers 150 is made of molybdenum disulfide-filled nylon.

In various embodiments, at least a portion of the vaginal vault retractor 100 is made of a metal material. As such, vaginal vault retractor 100 can be used in a sterile environment (e.g. an operating room, examination room, or otherwise). Due to its ability to be thoroughly cleaned and disinfected, metal provides advantages in that it can be reused and sterilized.

In various embodiments, one or more of the one or more of the pair of curved arms 120, perpendicular arm 140, and plurality of fingers 150 is constructed from a thermoplastic material, such as polycarbonate, polypropylene, polyethylene, and the like. Custom polymers and/or metal alloys and plating may be used for sliding surfaces and precision components like the hinge 130 and fastener 115. In various embodiments, the material used for the pin 115, the two curved arms 120, the hinge 130, the perpendicular arm 140, and plurality of fingers 150 include aluminum, cobalt-chromium alloys, stainless steel, titanium alloys, nickel plated aluminum, nickel-plated brass, VALROX®, and the like.

In various embodiments, one or more of the fasteners 115, the two curved arms 120, the hinge 130, the perpendicular arm 140, and plurality of fingers 150 is constructed from a nylon material, where nylon is a generic designation for a family of synthetic polymers composed of polyamides. Nylon is a strong, stiff engineering plastic with outstanding bearing and wear properties. Nylon can be used to replace metal parts, such as bearing, and the need for external lubrication. Nylon can be used to reduce the weight, noise, and wear of mating parts. In some embodiments, the color of the nylon use for one or more of the fastener 115, the two curved arms 120, the hinge 130, the perpendicular arm 140, and plurality of fingers 150 is white, green, blue, grey, or a combination thereof.

Nylon is available in several grades and a variety of special formulas. For example, nylon 6, nylon 6/6, and nylon 12. In various embodiments, the nylon used is an oil-filled nylon that eliminates the need for external lubrication and has enhanced wear properties. In some embodiments, the nylon used is $MoS_2$—molybdenum disulfide-filled nylon. MoS2 nylon eliminates the need for external lubrication and is often used in bearing and wear applications because of its superior strength and hardness.

In various embodiments, at least a portion of the vaginal vault retractor 100 is made of a nylon material. For example, nylon 6, nylon 6/6, an oil-filled nylon, and a molybdenum disulfide-filled nylon, and the like.

In various embodiments, at least a portion of the vaginal vault retractor 100 is made of a polyether ether ketone (PEEK) material.

In some embodiments, one or more of the fasteners 115, the two curved arms 120, the hinge 130, the perpendicular arm 140, and plurality of fingers 150 is made of a polyether ether ketone (PEEK) material. PEEK is a colorless organic thermoplastic polymer belonging to the polyaryletherketone (PAEK) family. PEEK's robustness makes it suitable for demanding applications. Synthesis of PEEK composites has further improved the antimicrobial, mechanical, and physicochemical properties of PEEK making PEEK well suited for bio-medical applications. The antimicrobial properties of PEEK are important for inhibiting or destroying the growth of microorganism and especially pathogenic microorganisms. For at least these reasons, PEEK is an important material for bio-medical applications.

In various embodiments, a method of manufacturing the vaginal vault retractor 100 comprises printing the vaginal vault retractor with a three-dimensional printer 100. In some embodiments, printing the vaginal vault retractor 100 comprises printing one or more of the pair of curved arms 120, the pair of perpendicular arms 140, the plurality of fingers 150, and the hinge 110, some of which may be fluidly coupled. The material used for the 3D printing may be a polyether ether ketone (PEEK) material. In some embodiments, the vaginal vault retractor 100 is manufactured using thermoforming or vacuum forming.

In various embodiments, the vaginal vault retractor 100 is made of a durable sanitary material, machine washable material that can be disinfected and sterilized using autoclaving, and the like. Autoclaving sterilizes a material using saturated steam under pressure. In various embodiments, the vaginal vault retractor 100 is disposable solution and the vaginal vault retractor 100 is recycled or safely disposed of to prevent infections and cross contamination between different patients.

In various embodiment, the method of manufacturing the vaginal vault retractor 100 comprises injecting a material into a mold of the vaginal vault retractor 100. In some embodiments, the mold of the vaginal vault retractor 100 comprises one or more of the pair of curved arms 120, the pair of perpendicular arms 140, the plurality of fingers 150, and the hinge 110, some of which may be fluidly coupled in the mold.

Figure 6B:
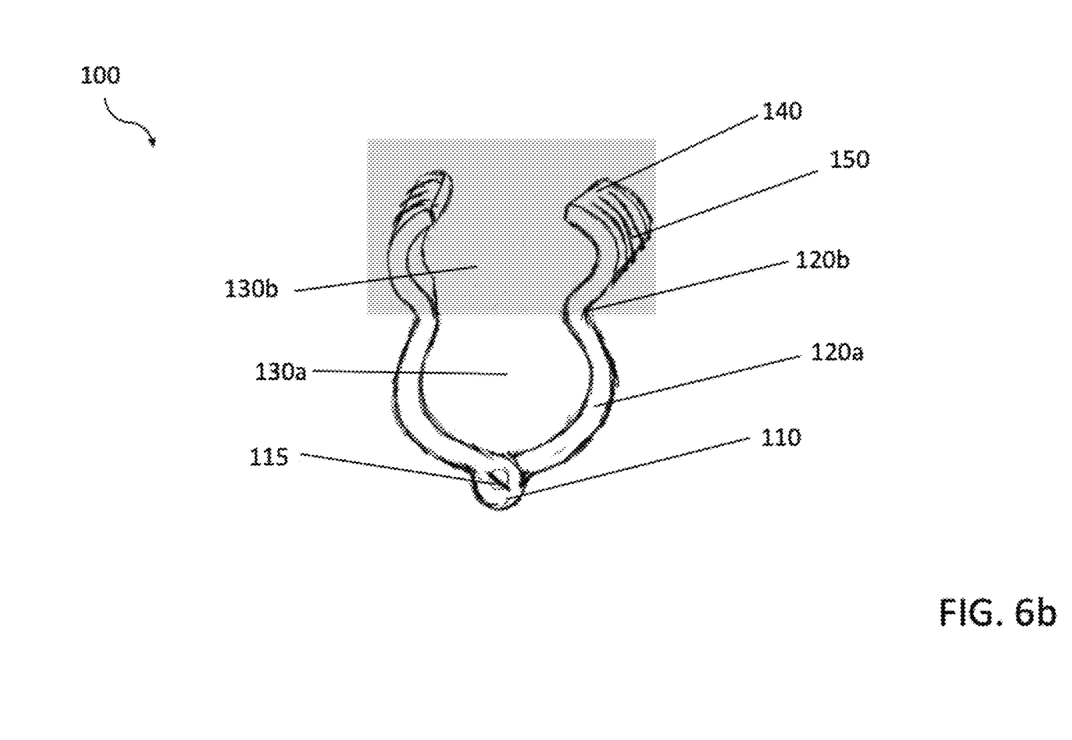
FIG. 6b illustrates the proposed vaginal vault retractor in the open position, in accordance with some embodiments described herein.

FIG. 6b shows the vaginal vault retractor 100 in the open position. In various embodiments, the vaginal vault retractor 100 is configured to open perpendicular to vagina canal 200, unlike convention speculums 10, which open parallel to the vagina canal 200. By opening laterally, underlying tissue of the vaginal vault 200 is exposed allowing for procedures such as repair of vaginal tears, episiotomies, vulvar and distal vaginal biopsies and excisional biopsies.

Friction is the resisting force between two surfaces that are sliding against each other. The friction is classified into two types: static friction and dynamic friction. Static friction is the force that resists the initial movement between the two static object, whereas dynamic friction or kinetic friction is the force that resists objects that are sliding against each other. The dynamic friction values are often lower than static friction values. If the coefficient of friction is low, near to zero, the two materials slide past each other easily. Whereas, if the coefficient is high, near to 1.0, the two materials do not slide past each other easily. If the material of the plurality of the fingers 150 of the upper portion 120b of the vaginal vault retractor 100 has a low coefficient of friction, then the vaginal vault retractor 100 is more likely to slide and fall than stay in place and be retained. If the material of the plurality of fingers 150 of the of the upper portion 120b of the vaginal vault retractor 100 has a high coefficient of friction, then the vaginal vault retractor 100 is more likely to stay in place and be retained than slide and fall than.

In various embodiments, an external surface of the vaginal vault retractor 100 is configured to have a smooth surface texture. In some embodiments, the external surface of the vaginal vault retractor 100 is covered in a plurality of smooth notches or indentations. The smooth notches have the effect of increasing the drag exerted on the underlying tissue, and thereby the friction between the two surfaces. The smooth notches are configured to prevent slippage of the underlying tissue while also gently and securely retaining the vaginal vault retractor 100 within the distal vagina 200.

In some embodiments, the external surface of the vaginal vault retractor 100 is covered in a plurality of smooth bumps. The smooth bumps are configured to prevent slippage of the underlying tissue while also gently and securely retaining the vaginal vault retractor 100 within the distal vagina 200. The smooth bumps have the effect of increasing the force exerted on the underlying tissue. Friction between two surfaces is increase if the two surfaces are pressed into each other with greater force. The smooth bumps have the effect of increasing the surface area that is in contact with the underlying tissue and thereby the friction.

In various embodiments, at least the plurality of fingers 150 of the upper portion 120b of the vaginal vault retractor 100 are, or coated in, a material having coefficient of friction that is high, that is about 0.4 or greater. For example, the high coefficient of friction material is a silicon, latex, nitrile rubber, rubber, and the like.

In various embodiments, at least the plurality of fingers 150 of the upper portion 120b of the vaginal vault retractor 100 have a surface texture to increase the static coefficient of friction. For example, at least the plurality of fingers 150 of the upper portion 120b were covered in one or more of fine, medium, and coarse knurled patterns, and the like, which enable the vaginal vault retractor 100 to obtain a better grip than if the surface were smooth.

In some embodiments, at least a lower portion or handles of the vaginal vault retractor 100 is a material configured to have a high coefficient of friction that makes the handles easier to grip and manipulate.

In various embodiments, the vaginal vault retractor 100 is coated with a material that enhances the durability and safety of the vaginal vault retractor 100. For example, the coating may have antimicrobial properties for inhibiting or destroying the growth of microorganism and especially pathogenic microorganisms.

In various embodiments, the vaginal vault retractor 100 is made of a material configured to reduce or prevent glare. In some embodiments, the material is a non-reflective material or has a surface finish that reduces or eliminates glare.

The foregoing is provided for purposes of illustrating, explaining, and describing embodiments of this disclosure. Modifications and adaptations to these embodiments will be apparent to those skilled in the art and may be made without departing from the scope or spirit of this disclosure.

Although the subject matter has been described in terms of exemplary embodiments, it is not limited thereto. Rather, the appended claims should be construed broadly, to include other variants and embodiments, which may be made by those skilled in the art.

We claim:

1. A vaginal vault retractor comprising:
   a hinge;
   a pair of curved arms, wherein each of the pair of curved arms comprises a lower portion and an upper portion, wherein a near end of the lower portion of each of the pair of curved arms is coupled to the hinge;
   a pair of perpendicular arms, wherein a near end of each of the pair of perpendicular arms is coupled to the distal end of the upper portion of the each of the pair of curved arms; and
   a plurality of fingers emulating from each pair of perpendicular arms,
   wherein one or more of the pair of curved arms, the pair of perpendicular arms, the plurality of fingers, and the hinge is made of a nylon material, and wherein the nylon material is one or more of nylon 6, nylon 6/6, nylon 12, and wherein the hinge is made of one or more of oil-filled nylon and molybdenum disulfide-filled nylon; and
   wherein the pair of curved arms form a pair of oval apertures, wherein the pair of oval apertures comprises a lower oval aperture that is proximate to the hinge and an upper oval aperture that is distal to the hinge, wherein the lower oval aperture and the upper oval aperture are in fluid communication, and wherein a size of the lower oval aperture is larger than a size of the upper oval aperture.

2. The vaginal vault retractor of claim 1, wherein the lower portion each of the pair of curved arms is operable to rest on a perineum and provide and an unobstructed view of a vaginal vault, and wherein the plurality of fingers emulating from each pair of the perpendicular arms are operable to be placed within the vaginal vault.

3. The vaginal vault retractor of claim 2, wherein each of the plurality of fingers has a shape that is the same as a shape of the upper portion of each of the pair of curved arms.

4. The vaginal vault retractor of claim 2, wherein the pair of curved arms are operable to open perpendicular to the vaginal vault.

5. The vaginal vault retractor of claim 2, wherein the hinge is operable to be located below the vaginal vault, and wherein the hinge is operable to be located above the vaginal vault.

6. The vaginal vault retractor of claim 2, wherein a shape of the plurality of fingers emulating from each pair of perpendicular arms are operatable to increase a static coefficient of friction between the plurality of fingers and the vaginal vault, and wherein the plurality of fingers emulating from each pair of perpendicular arms form a linear series of elongated ridges.

7. The vaginal vault retractor of claim 1, wherein each of the plurality of fingers is made of a material having a high coefficient of friction.

8. The vaginal vault retractor of claim 1, wherein one or more of the pair of curved arms, the pair of perpendicular arms, and the plurality of fingers is made of a polyether ether ketone (PEEK) material, and wherein the PEEK material is operable to have antimicrobial properties.

9. The vaginal vault retractor of claim 1, wherein one or more of the pair of curved arms, the pair of perpendicular arms, the plurality of fingers, and the hinge is made of a thermoplastic material, and wherein the thermoplastic material is one or more of polycarbonate, polypropylene, and polyethylene.

10. The vaginal vault retractor of claim 1, wherein the pair of curved arms form a lemniscate shape, and wherein the lemniscate shape has a gap in a middle when the pair of curved arms are in a closed position.

11. The vaginal vault retractor of claim 1, wherein the lower portion of each of the pair of curved arms forms a handle, and wherein the handle is coated with a material having a high coefficient of fiction operable to make the handle easier to grip and manipulate.

12. The vaginal vault retractor of claim 11, wherein a portion of the handle extends beyond the hinge to form an extended handle, and wherein the extended handle comprises a loop operable to make the extended handle easier to grip and manipulate.

13. The vaginal vault retractor of claim 1, wherein the hinge further comprises a frictional brake, wherein the pair of curved arms have a range of rotation of 90 degrees and below, and wherein the frictional brake is operable to clamp the pair of curved arms in a static position within the range of rotation.

14. The vaginal vault retractor of claim 13, wherein the frictional brake comprises a locking screw, wherein the locking screw is operable to adjust a level of friction for the hinge, and wherein the locking screw is operable to clamp the pair of curved arms in a static position within the range of rotation.

15. The vaginal vault retractor of claim 1, wherein the hinge comprises one or more of a leaf spring, a torsion, and a web operable to push the pair of curved arms to an open position.

16. The vaginal vault retractor of claim 1, wherein the hinge comprises a stop operable to arrest a rotation of the pair of curved arms.

17. A vaginal vault retractor comprising:
    a hinge, wherein the hinge comprises a first hinged member having a pair of spaced-apart knuckles and a second hinged member having a single knuckle operable to fit between the pair of spaced-apart knuckles;
    a first curved handle having a first near end couped to the first hinged member and a second curved handle having a second near end coupled the second hinged member, wherein the first curved handle and the second curved handle form an aperture with an hourglass shape having a bust and a hip, and wherein a size of the bust is greater than a size of the hip; and
    a first wing coupled to a first distal end of the first curved handle and a second wing coupled to a second distal end of the second curved handle.

18. A vaginal vault retractor comprising:
    a pair of hinged curved arms having a near end and a distal end, wherein the pair of hinged curved arms form a shape of an upright lemniscate, and wherein the pair of hinged curved arms are flexibly coupled by a hinge at the near end of each of the pair of hinged curved arms;
    a perpendicular arm having plurality of fingers coupled the distal end of each of the pair of hinged curved arms; and
    a locking screw, wherein the locking screw is operable to adjust a level of friction for a rotation of the pair of hinged curved arms, and wherein the locking screw is operable to arrest the rotation of the pair of hinged curved arms, wherein the pair of hinged curved arms form a pair of oval apertures, wherein the pair of oval apertures comprises a lower oval aperture that is proximate to the hinge and an upper oval aperture that is distal to the hinge, wherein the lower oval aperture and the upper oval aperture are in fluid communication, and wherein a size of the lower oval aperture is larger than a size of the upper oval aperture.

* * * * *